United States Patent
Prins

[19]

[11] Patent Number: 5,577,912
[45] Date of Patent: Nov. 26, 1996

[54] ADJUSTABLE IMPLANT FIXTURE

[76] Inventor: Steven P. Prins, 1250 Peach St., Suite M, San Luis Obispo, Calif. 93401

[21] Appl. No.: 308,275

[22] Filed: Sep. 19, 1994

[51] Int. Cl.$^6$ .................. A61C 13/12; A61C 13/225; A61C 8/00
[52] U.S. Cl. ........................... 433/172; 433/173
[58] Field of Search ........................ 433/172, 173, 433/174, 175, 176

[56] References Cited

U.S. PATENT DOCUMENTS

| | | | |
|---|---|---|---|
| 3,732,621 | 5/1973 | Bostrom | 433/174 |
| 4,907,969 | 3/1990 | Ward | 433/173 |
| 4,932,868 | 6/1990 | Linkow et al. | 433/174 |
| 5,007,835 | 4/1991 | Valen | 433/174 |
| 5,073,111 | 12/1991 | Daftary | 433/173 |
| 5,116,225 | 5/1992 | Riera | 433/173 |

Primary Examiner—Nicholas D. Lucchesi
Attorney, Agent, or Firm—James B. Middleton

[57] ABSTRACT

A fixture for attaching a dental prosthesis to a dental implant has a base to be received on the implant, and a head attachable to the base. The base has an angled upper surface, and the head has an angled lower surface, the head being selectively rotatable with respect to the base. As a result, the head can be disposed with respect to the base so that the head will always be perpendicular to the gum line, even though the implant is angled with respect to the gum line. A non-round projection on the head engages a non-round recess on the base to prevent rotational movement when the fixture is installed, and a single screw extends through the head, through the base, and into the implant to hold the assembly together.

4 Claims, 1 Drawing Sheet

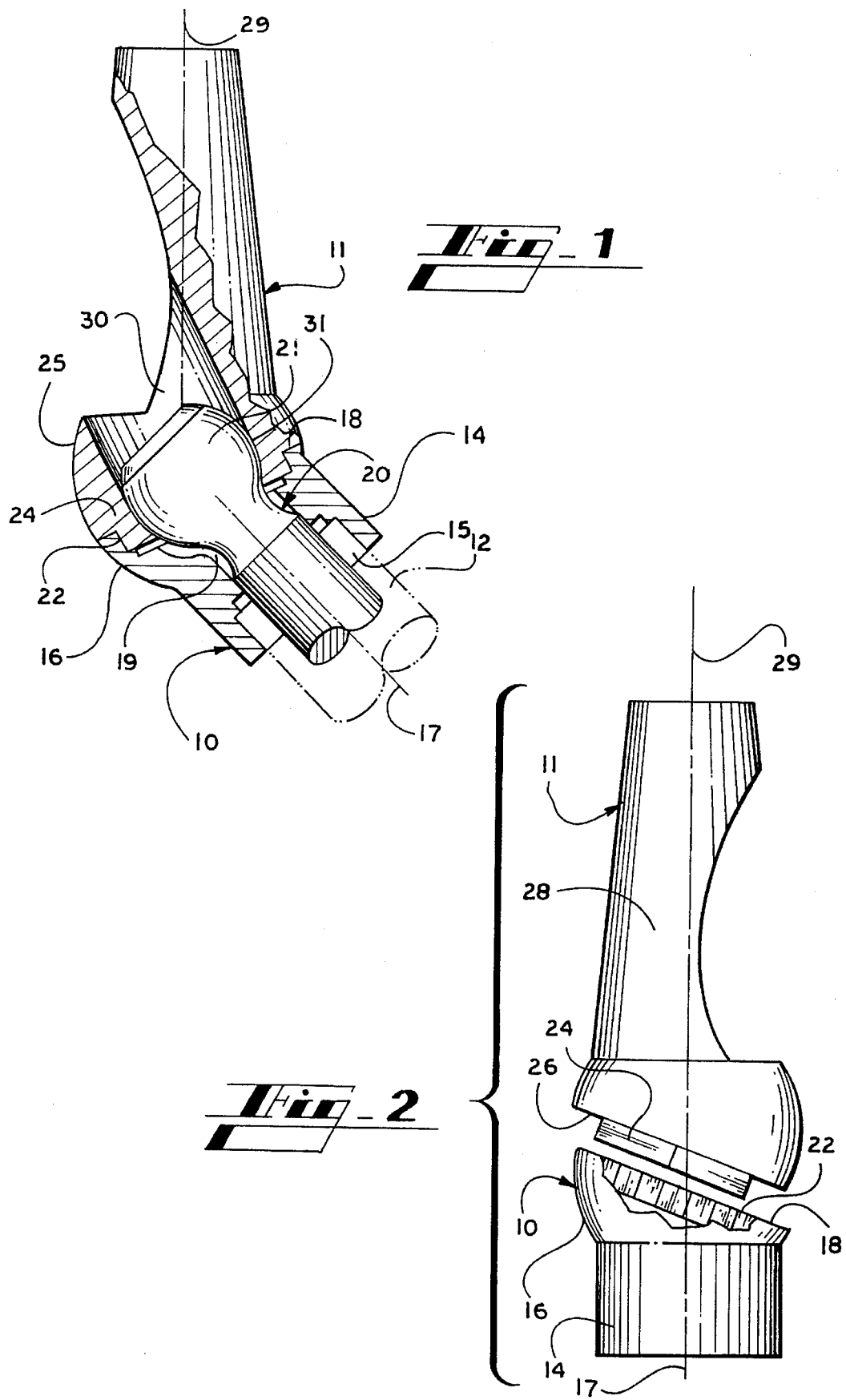

ADJUSTABLE IMPLANT FIXTURE

BACKGROUND OF THE INVENTION

1. Field of the Invention

This invention relates generally to restorative dentistry, and is more particularly concerned with an adjustable fixture to be attached to a dental implant.

2. Discussion of the Prior Art

It is well known in the art as a means to replace a missing tooth, or some missing teeth, to place an implant into the bone, extending close to the gum line. A prosthesis is then attached to the implant, so the prosthesis is substantially permanent. When the implant is installed along a line coaxial with the centerline of the intended prosthesis, a simple fixture provides for attachment of the prosthesis to the implant.

When an implant is installed, one must drill a hole into the bone, the implant then being screwed, or driven, into the hole. Due to the anatomy of the body, however, one frequently cannot drill the ideal hole to receive the implant. For example, the ideal hole for the implant may sometimes protrude through the surface of the bone. Similarly, the ideal hole may extend into one of the facial sinuses. In each case, the hole for the implant must be angled to be sure the entire implant is within the bone.

Though an angled hole for the implant solves the problem of perforating the bone surface, it creates another problem in that the prosthesis to be attached to the implant will also be angled, which will be unacceptable. As a result, a more complex fixture is required in order to align the prosthesis properly in the dental arch in spite of one or more angled implants.

There is a very elaborate fixture system made by Universal Implant Systems, Inc., in Washington, D.C., but this system is quite complex, including perhaps six separate pieces for a single tooth. Even so, the final step is to make a custom casting for use with the system. Also, if the implant is angled, the correction requires selection of one of a plurality of angled pieces in an effort find a complementarily angled piece so the prosthesis will be straight. The dentist is therefore required to have a sufficient inventory to include all the pieces that may be needed for any given patient.

SUMMARY OF THE INVENTION

The present invention provides an adjustable fixture including a base to be received directly on the implant, and a head to be selectively received on the base. The upper surface of the base and the lower surface of the head are angled, so rotation of the head with respect to the base will change the angle of the centerline of the head. In the preferred embodiment of the invention, a single screw fixes the head to the base and fixes the base to the implant.

In one embodiment of the invention, the surfaces of the base and the head are angled at twenty degrees, so the maximum angle between the two is forty degrees, and the minimum angle is zero degrees. To prevent inadvertent rotation, the head includes a hexagonal protrusion, and the base defines a twelve-point recess. As a result, the head can be rotated in thirty degree increments. This thirty degrees of rotation will yield a change in orientation of the centerline of the head of about seven degrees.

BRIEF DESCRIPTION OF THE DRAWINGS

These and other features and advantages of the present invention will become apparent from consideration of the following specification when taken in conjunction with the accompanying drawings in which:

FIG. 1 is a longitudinal cross-sectional view showing a head mounted on a base in accordance with the present invention, angled at the maximum angle; and, FIG. 2 is a front elevational view showing the base and head exploded, and in position for zero angle.

DETAILED DESCRIPTION OF THE EMBODIMENT

Referring now more particularly to the drawings, and to that embodiment of the invention here presented by way of illustration, the embodiment of the invention shown in FIG. 1 includes a base 10 and a head 11. As illustrated in FIG. 1, the implant indicated in phantom at 12 is at an angle to the vertical, so the base 10 is also at an angle to the vertical because the base 10 is received directly on the implant 12. The head 11 is received directly on the base 10, but it will be noticed that the head 11 extends substantially vertically from the base 10. The vertical orientation of the head 11 is possible because of the angled surfaces of both the base 10 and the head 11.

In more detail, the base 10 has a generally cylindrical body 14 defining a recess 15 at its lowermost end. The shape of the recess 15 is not here shown in detail, but it will be understood by those skilled in the art that the recess 15 will be shaped to receive the upper end of an implant, such as the implant 12. It is common that implants have a non-round upper end so a fixture received thereon is mechanically locked against rotation. The non-round shape may take any form, and the recess 15 of the present invention will be formed to match the intended implant, or group of implants.

The upper end of the base 10 is spherical in form, as at 16, intersecting with the cylindrical body 14. The uppermost edge 18 of the spherical portion 16 is in a single plane, but the plane is angled with respect to the centerline 17 of the body 14.

Centrally of the base 10, there is a hole 19 for receiving a screw 20. The screw 20 has a generally spherical head 21 which will be discussed in more detail hereinafter. The uppermost end of the base 10 defines a non-round opening 22 for receiving a projection 25 from the head 11. While virtually any non-round configuration may be used, it is important for the present invention that the projection 24 be incrementally rotatable with respect to the opening, or recess, 22. Thus, in the embodiment of the invention here presented, the projection 24 is hexagonally shaped, and the opening 22 is twelve-pointed. As a result, the hexagon 24 can be received by the opening 22 at a plurality of rotational positions that are 30° apart.

While the opening, or recess, 22 has twelve points, it is not in the form of a dodecagon; rather, it is in the form of two hexagons that have been rotated with respect to each other, giving twelve "points" but not twelve sides in the usual geometric sense. The twelve pointed shape is well known in the twelve pointed socket wrenches, and those skilled in the art will understand without further discussion.

The lowermost end of the head 11 is formed as a sphere as at 25, the sphere 25 having the same radius as the sphere 16; and, the bottom surface 26 is angularly disposed with respect to the body 28. As with the base 10, the bottom surface is in a single plane, but that plane is angularly disposed with respect to the centerline 29 of the head 11.

With attention particularly to FIG. 2 of the drawings, it can be seen that the head 11 has a body 28 which will receive a prosthesis directly thereon as is well known to those skilled in the art. The centerline 29 of the body 28 will generally be substantially perpendicular to the bone, or to the gum surface where the prosthesis is to be installed. For this reason, the position of the fixture shown in FIG. 2 is considered "normal", and relative terms such as "top" "bottom" etc will be used with this reference, and such terms are not intended to be limitations, but only explanations.

The base 10 and head 11 are two separate pieces; and, these two pieces must be fixed to the implant 12. In the present invention, a single screw 20 fixes the three pieces together. The opening 19 in the base 10 has already been discussed, and the opening 30 in the head 11 is shown in FIG. 1 of the drawings. The hole 30 is angularly disposed with respect to the centerline 29, but the hole 30 is perpendicular to the plane of the lowermost surface 26. The hole 30 has a diameter to just receive the spherical head 21 of the screw 20; and, the lower end of the hole 30 curves inward at 31. The inward curve 31 is preferably spherical so the head 21 and the curved hole 31 will match. It will therefore be understood that the head 11 can be positioned at many different angles and still held snugly by the screw 20.

With the above and foregoing description in mind, it will be understood that the present invention provides a very simple and easy-to-use fixture to be attached to a dental implant, regardless of the angle of the implant. The base 10 of the present device will be slipped onto the implant, and the upper portion of the base 10 will be somewhat above the gum line. The head 11 will then be placed on the base 10. The surface 18 of the base 10 is at a 20° angle with respect to the centerline 17, and the surface 26 is at a 20° angle with respect to the centerline 29. As a result, if the base 10 and the head 11 are oriented as shown in FIG. 2, the centerlines 17 and 29 will be co-axial, and the prosthesis on the body 28 will be in line with the implant 12.

Assuming the opposite extreme, if the base 10 and head 11 are oriented as shown in FIG. 1, there will be a 40° angle between the centerline 17 and the centerline 29. Since the head 11 can be rotated in increments with respect to the base 10, the angle between the centerlines 17 and 29 can be varied. One will therefore determine the proper orientation to place the prosthesis in the preferred position. When the device is ready to be fixed in place, the screw 20 will be placed through the hole 30 and into position as shown in FIG. 1. Though it is not here shown, those skilled in the art will understand that such screws normally have a receptacle for an Allen wrench to allow rotation of the screw.

It will of course be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

I claim:

1. An implant fixture for fixing a dental prosthesis to a dental implant, said fixture comprising a base receivable on the implant and a head selectively receivable on said base, said base including a body having a centerline, said body defining a cavity concentric with said centerline of said body for receiving the implant, said base further including an upper surface in a plane that is angularly related to said centerline of said body said head including a body having a centerline, said body of said head being adapted to receive a dental prosthesis thereon, said head further including a lower surface in a plane that is obliquely angularly related to said centerline of said body of said head, and means for fixing said head to said base and for fixing said fixture to the implant, said body of said head defining a hole therein, said hole extending perpendicularly to said lower surface of said body of said head, and including a screw receivable in said hole, said hole including a spherical constriction adjacent to said lower surface, said screw including a spherical head receivable within said constriction so that said head and said screw can move relative to each other.

2. An implant fixture, for fixing a dental prosthesis to a dental implant, said fixture comprising a base receivable on the implant and a head selectively receivable on said base, said base including a body having a centerline, said body defining a cavity concentric with said centerline of said body for receiving the implant, said base further including an upper surface in a plane that is angularly related to said centerline of said body, said head including a body having a centerline, said body of said head being adapted to receive a dental prosthesis thereon, said head further including a lower surface in a plane that is obliquely angularly related to said centerline of said body of said head, and means for fixing said head to said base and for fixing said fixture to the implant, and further including a projection extending from said lower surface of said body of said head, said base defining a recess for receiving said projection, said projection and said recess being non-round for preventing rotation of said head with respect to said base when said projection is received within said recess.

3. An implant fixture as claimed in claim 2, wherein said projection is in the shape of a regular polygon so that said projection can be received within said recess in a plurality of rotational positions.

4. An implant fixture as claimed in claim 3, wherein said projection is hexagonal, and said recess is a twelve pointed recess.

* * * * *